US006693205B2

(12) United States Patent
Justice

(10) Patent No.: US 6,693,205 B2

(45) Date of Patent: Feb. 17, 2004

(54) PROCESS FOR PREPARING OPTICALLY ACTIVE EPOXIDES

(75) Inventor: David Edward Justice, Chester (GB)

(73) Assignee: Phoenix Chemicals Limited, Bromborough (GB)

( * ) Notice: Subject to any disclaimer, the term of this patent is extended or adjusted under 35 U.S.C. 154(b) by 40 days.

(21) Appl. No.: 10/332,608

(22) PCT Filed: Sep. 18, 2001

(86) PCT No.: PCT/GB01/04146

§ 371 (c)(1), (2), (4) Date: Jan. 10, 2003

(87) PCT Pub. No.: WO02/24671

PCT Pub. Date: Mar. 28, 2002

(65) Prior Publication Data

US 2003/0171603 A1 Sep. 11, 2003

(30) Foreign Application Priority Data

Sep. 18, 2000 (GB) ............................................ 0022772

(51) Int. Cl.[7] ............................................ C07D 301/02

(52) U.S. Cl. ...................................................... 549/518

(58) Field of Search ......................................... 549/518

(56) References Cited

FOREIGN PATENT DOCUMENTS

| | | | |
|---|---|---|---|
| EP | 0 657 446 A1 | | 6/1995 |
| EP | 1 029 856 A | | 8/2000 |
| EP | 1 029 856 A1 | * | 8/2000 |
| JP | 09/323960 | | 3/1998 |
| WO | WO 99/38855 A | | 8/1999 |
| WO | WO 00/44736 A | | 8/2000 |

OTHER PUBLICATIONS

Reference Supplied by Applicant.*

PCT International Search Report (PCT/GB 01/04146).

Aguilar, N. et al. "A Convergent, Stereocontrolled Synthesis of C2–Symmetrical and Pseudosymmetrical Sulfur–Tethered Bis (amino alcohols)" Tetrahedron Letters, NL., Elsevier Science Publishers, Amsterdam, vol. 40, No. 20, May 14, 1999, pp. 3913–3916, XP004163779; ISSN: 0040–4039.

Pegorier, L. et al. "A General Stereocontrolled Synthesis of Hydroxyethylene Dipeptide Isosteres" Tetrahedron Letters, NL, Elsevier Science Publishers, Amsterdam; vol. 36, No. 16, Apr. 17, 1995, pp. 2753–2756, XP004028345; ISSN: 0040–4039.

Beier C., et al.: "The First Asymmetric Synthesis of (1R.1's)–1–(1'–(benzyloxy–carbonyl–methylamino)–2–'phenylethyl) oxirane: a promising building block for the synthesis of peptide mimics" Synlett., No. 1, Jan. 1998 (1998–01), pp. 41–42, XP002154607 Thieme Verlag, Stuttgart., De ISSN: 0936–5214.

O. Mitsunobu: "The Use of Diethyl Azodicarboxylate and Triphenylphosphine in Systhesis and Transformation of Natural Products" Synthesis, De, George Thieme Verlag, Stuttgart, 1981, pp. 1–28; XP002123593; ISSN: 0039–7881.

* cited by examiner

*Primary Examiner*—Amelia Owens
(74) *Attorney, Agent, or Firm*—Brooks Kushman P.C.

(57) ABSTRACT

The invention concerns a process for the production of optically active epoxides useful as pharmaceutical intermediates, particularly in the field of HIV protease inhibitors. The optically active epoxides are produced in commercially acceptable yields from an optically active alcohols by a Mitsunobu reaction and a cyclisation step, preferably comprising an intermediate re-crystallisation step. The stereochemistry of the alcohol is inverted during the Mitsunobu reaction to produce the desired epoxide.

17 Claims, No Drawings

PROCESS FOR PREPARING OPTICALLY ACTIVE EPOXIDES

This application is a 371 of PCT/GB01/04146 filed Sep. 18, 2001.

BACKGROUND OF THE INVENTION

Field of the Invention

The present invention concerns a process for producing optically active epoxides, particularly those epoxides which are useful as pharmaceutical intermediates There are a number of potential pharmaceutical products which contain the following optically active grouping:

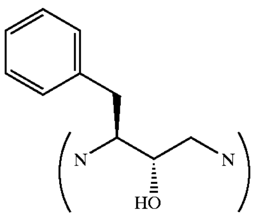

The enantiomer (2S, 3R) of this grouping may also be useful in pharmaceutical compounds. The grouping is derivable from the epoxide of equivalent stereochemistry, in the case of the (2R, 3S)-grouping, the (2R, 3S)-epoxide:

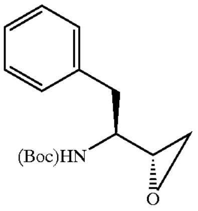

where Boc is a butoxycarbonyl amine protecting group.

SUMMARY OF THE INVENTION

EP-A-0885879 describes a process for producing optically active cyanohydrins, particularly an optically active N-(protected)-3-amino-2-hydroxy-4-phenylbutyronitrile which comprises treating a mixture of diastereomers of an N-protected)-3-amino-2-bydroxy-4-Aphenylbutyronitrile in the presence of an amine and an organic solvent. The optically active compound is said to be an intermediate in the production of certain pharmaceutical compounds.

EP-A-0934923 describes a method for producing optically active erythro-3-amino-2-hydroxybutyric esters comprising oxidising the hydroxyl group at the 2-position of an optically active (at the 3-position) 3-amino-2-hydroxybutyric ester and then reducing erythro-selectively the resulting product using alubnum alkoxide. The resulting optically active compound is said to be a pharmaceutical intermediate, specifically for HIV protease inhibitors.

WO-A-99/38855 describes a process for producing optically active threo-3-amino-1,2-epoxy compounds comprising subjecting an optically active threo-3-amino-1,2-diol to allkylsulphonylation or arylsulphonylation in an organic solvent in the presence of a base to give the corresponding optically active threo-3-amino-2-hydroxy-1-sulphonyloxy compound and subjecting the resulting compound to epoxidation in the presence of a base to give the corresponding optically active threo-3-amino-1,2-epoxy compound.

WO-A-00/10986 describes a process for the preparation of (2R,3S)-3-amino-1,2-oxirane comprising treating a (2S, 3S)-3-amino-1-halo-2-hydroxy-4-phenylbutane or a (2S, 3S3-amino-4-phenylbutane-1,2-epoxide either with a quaternary ammonium carboxylate or with both a metal carboxylate and a quaternary ammonium salt to prepare a (2S,3S)-1-acyloxy-3-amino-2-hydroxy-4-phenylbutane, treating this compound with a sulphonyl halide in the presence of an organic base to prepare a (2S,3S)-1-acyloxy-3-amino-2-sulphonyloxy-4 phenylbutane and subjecting the compound thus obtained to treatment with an inorganic base. It is said that this process allows the production of intermediates for HIV protease inhibitors using L-phenylalanine as a raw material.

U.S. Pat. No. 5,936,104 describes a process for producing (2S,3S)- or (2R,3R)-1,2epoxy-3-amino-4phenylbutane derivatives comprising treating a 1-halo-2-hydroxy-3-amino-4-phenylbutane derivative with a base in an aprotic polar organic solvent or a mixed solvent composed of an aprotic polar organic solvent and water and then causing the resulting epoxide to crystallise out from a mixed solvent composed of an aprotic polar organic solvent and water. The resulting compound is said to be useful as an intermediate in the production of various HIV protease inhibitors as described, for example, in Japanese Kokai Publication Hei-08-109131.

WO-A-95/08530 describes a process for producing 3-amino-2-hydroxy-1-propanol derivatives which are said to be useful as intermediates in the production of medicines.

JP9323960 describes a method for obtaining 3-amino-1, 2-oxirane by using a 3-amino-1,2-diol as a raw material. The process comprises reacting an N-(protected)-3-amino-1,2-diol with an orthoacetate or orthoformate in the presence of an acid catalyst to form an alkoxyalkylidene. The alkoxyalkylidene is reacted with a halogenating agent to form an alkoxy halide which is then treated with a base and converted to an epoxide, thus obtaining the 3-amino-1,2-oxirane.

WO-A-97/42180 describes a process for preparing oxiranemethanamine derivatives, which are said to be usefull as intermediates for preparing aspartyl protease inhibitors, comprising the steps of activating an aminodiol, acylating the aminodiol and reacting the acylated aminodiol with a base to form an epoxy compound.

The processes and methods described in these documents all suffer from one or more of the following disadvantages: they do not describe methods of synthesising 2R,3S-epoxides or their enantiomers; their stereochemistry is unclear; they use expensive or difficult to obtain reagents; they describe complex reaction procedures with numerous stages; they describe low product yields; the products described are insufficiently pure for use as pharmaceutical intermediates; they relate to laboratory scale processes and are of unproven or uncertain value on a commercial scale; or they are commercially unattractive for other reasons.

The academic literature describes various methods of synthesising 2R,3S-epoxides but these also suffer from one or more of the aforesaid disadvantages or disclose mixtures of epoxides with other stereoisomers. Examples of such academic literature include Ojima et al, Tetrahedron Letters 39 (1998) 923–926; Barrish et al, J. Med.Chem. 1994, 37, 1758–1768; Romeo and Rich, Tetrahedron Letters, 35 (1994) 4939–4942; Luly et al, J.Org.Chem. 1987, 52, 1487–1492; Evans et al, J.Org.Chem. 1985, 50,4615–4625 and Parkes et al, J.Org.Chem. 1994, 59, 3656–3664.

Other attempts to find commercially acceptable routes to the 2S,3S- and 2R,3S-epoxides have been made recently by Malik, whose work in this respect was detailed at the 3rd International Conference "Organic Process Research and Development" organised by Scientific Update on 10–12 July 2000. However, the yields for individual steps described are poor (about 53%) and toxic and/or expensive chemicals, such as cesium acetate and 18-crown ether, are used.

There remains a need in the art for an improved process for the production of optically active epoxide pharmaceutical intermediates.

According to the present invention there is provided a process for producing an optically active (2R, 3S)-epoxide of the general formula (1):

(1)

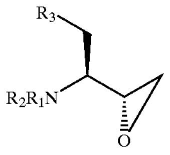

or its enantiomer wherein each of $R_1$ and $R_2$ is independently selected from hydrogen, optionally substituted alkyl, aryl, aralkyl or alkaryl groups, and amine-protecting groups and $R_3$ is selected from hydrogen and optionally suitably protected alkyl, cycloalky, aryl, aralkyl or alkal groups which comprises conducting a Mitsunobu reaction on an optically active (2S,3S)-alcohol of general formula (2):

(2)

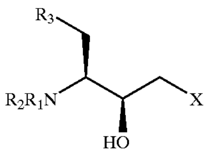

or its enantiomer wherein X is a leaving group and $R_1$, $R_2$ and $R_3$ are the same as the corresponding $R_1$, $R_2$ and $R_3$ in formula (1) and cyclising the resulting Mitsunobu product

DESCRIPTION OF THE PREFERRED EMBODIMENTS

The Mitsunobu process has been known since 1967 (Mitsunobu and Yamada in M.Bull.Chem.Soc.JPN. 1967, 40, 2380–2382) and was later described in 1991, the general reference being Mitsunobu, Synthesis, 1981, 1–28. This document described intermolecular dehydration reactions between alcohols and acidic components on treatment with diethyl azodicarboxylate and triphenylphosphine in which virtually complete inversion of the configuration of the alcoholic hydroxy group takes place. The Mitsunobu process was reviewed by Hughes, Org.Reac. 1992, 42, 335. Mechanistic studies of Mitsunobu chemistry have been described by Camp and Jenkins in J.Org.Chem. 1989, 54, 3045–3049, Varasi et al in J.Org.Chem. 1987, 52, 4235–4238 and Hughes et al in J.Am.Chem.Soc 1988, 110, 6487–649. The effect of the acidic component in Mitsunobu chemistry has been described by Martin and Dodge in Tetrahedron Letters, 1991, Vol. 32 No. 26, pages 3017–3020, by Dodge et al in J.Org.Chem. 1994, 59, 234–236 and by Hughes and Reamer in J.Org.Chem. 1996, 61, 2967–2971. Examples of industrial processes utilising Mitsunobu chemistry are described by Thomas et al in Organic Process Research and Development 1997, 1, 294–299 and by Marzoni et al in Synthetic Communications, 25 (16), 2475–2482 (1995). Reference to the use of a Mitsunobu reaction for the synthesis of substituted piperazinones can be found in WO-A-00/01678.

A preferred process according to the invention, comprises recrystallising the Mitsunobu reaction product prior to cyclising. $R_3$ is preferably a group selected from hydrogen and optionally substituted alkyl, cycloaukyl, aryl, arallcyl and alkaryl groups. The group is preferably protected where it contains free oxygen, nitrogen or sulphur, which may react with reagents used in the Mitsunobu reaction.

The leaving group X is any suitable leaving group and is preferably selected from halogens, sulphonate esters and trialkyl ammonium groups.

One reaction scheme according to the invention may be summarised as follows:

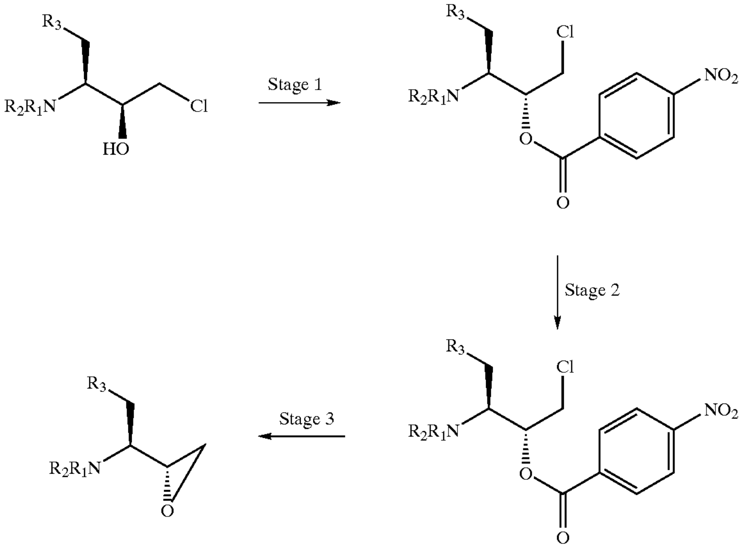

Estenification Step

The esterification step preferably comprises treating the compound of formula (2) with a phosphine and an azodicarboxylate under acid conditions to form an intermediate ester of formula (3):

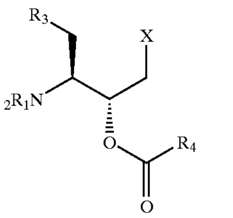

(3)

wherein X, $R_1$, $R_2$ and $R_3$ are the same as the corresponding X, $R_1$, $R_2$ and $R_3$ in formula (2) and $R_4$ is an optionally nitrogenated alkyl, aryl, aralkyl or alkaryl group.

Suitable phosphines include trialkyl- and triaryl phosphines such as triphenylphosphine, tributylphosphine and methyldiphenylphosphine. Triphenylphosphine is preferred. Polymer bound triphenylphosphine as disclosed in J. Org. Chem, 1983, 48, 3598 may also be used, as may bis (diphenylphosphine)ethane disclosed in Tetrahedron Letters, 1998, 39, 7787.

Suitable azodicarboxylates include diisopropylazodicarboxylate (DIAD), diethylazodicarboxylate (DEAD) and di-tert-butylazodicarboxylate (DTBA). DIAD is preferred.

Suitable acids include carboxylic acids such as acetic acid, trifluoroacetic acid and para-nitrobenzoic acid (PNBA). PNBA is preferred.

Suitable solvents for the esterification are aprotic solvents including benzene, toluene, chlorinated hydrocarbons, ethyl acetate and water miscible solvents including tetrahydrofuran, dimethoxyethane and dioxane. Toluene and tetrahydrofuran are preferred. Suitable solvents for crystalisation of the esterified product include low boiling alcohols, optionally in admixture with water. Ethanol/water mixtures are preferred.

Recrystallisation Step

The recrystallisation step is preferably effected from an ethanol/water mixture and is conducted to remove minor contaminants of triphenylphosphineoxide, DIAD-H2 and of 2S,3S-ester from the 2R,3S-ester (or 2R, 3R-ester from the 2S, 3R-ester in the enantiomerically equivalent process of the invention).

Cyclisation Step

The cyclisation step preferably comprises treating the recrystallised intermediate ester with an aqueous base. Suitable bases include alkali and alkaline earth metal hydroxides and quaternary ammonium or phosphonium compounds. The 2R,3S-ester intermediate can be saponified and cyclised by, for example, working up in ethanol and an aqueous base such as potassium hydroxide. Phase transfer conditions can also be employed using an aqeuous base, a water immiscible solvent, such as toluene or a chlorinated hydrocarbon, and a suitable catalyst, such as a quaternary ammonium or phosphonium salt.

The alcohol of formula (2) may be obtained by known routes (e.g. J. Org. Chem. 1994, 59, 3656) from amino acids and synthetic amino acids. One preferred starting material for obtaining the 2R, 3Sepoxide is L-phenylalanine. A preferred starting material for obtaining the 2S, 3R-epoxide is D-phenylalanine. In the process of the invention, the alcohol is preferably a haloalcohol, even more preferably a chloroalcohol.

The amine protecting group is preferably butoxycarbonyl or benzyloxycarbonyl.

The invention will now be more parxicularly described with reference to the following examples.

EXAMPLE 1

A 3 (protected) amino4-phenyl-1-chlorobutan-2-ol was esterified according to the following reaction scheme:

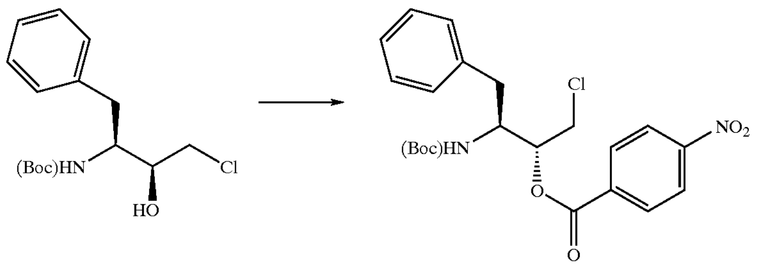

Reagents

| Reagents | Mass | Strength | 100% Strength | MW | Moles | Eq. | Source |
|---|---|---|---|---|---|---|---|
| 2S,3S chloroalcohol | 30.0 g | 96.9% 2S,3S | 29.1 g | 300 | 0.097 | 1.0x | Synthesised according to J. Org. Chem. 1994, 59, 3656 |
| DIAD | 24.6 g | 95% | 23.4 g | 202 | 0.116 | 1.2x | Aldrich PO 06304DR |
| Triphenylphosphine (TPP) | 30.6 g | 99% | 30.3 g | 262 | 0.116 | 1.2x | Aldrich 60707009 |
| p-Nitrobenzoic acid (PNBA) | 20.2 g | 98% | 19.8 g | 167 | 0.119 | 1.2x | Aldrich 07117HU |
| Toluene | 1200 ml | >99% | 1200 ml | 92 | — | — | BDH 30454 |
| Ethanol | 450 ml | Absolute | 450 ml | 85 | — | — | Hays DEB100 |
| Water | 180 ml | Towns | 180 ml | 18 | — | — | Towns |
| Ethanol/Water | 100 ml | Absolute/ | 1:1 | — | — | — | Hays DEB 100/ |

-continued

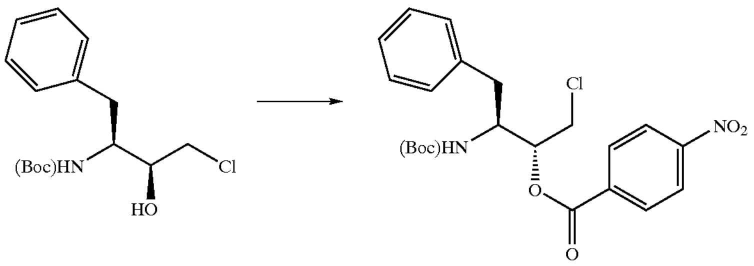

Reagents

| Reagents | Mass | Strength | 100% Strength | MW | Moles | Eq. | Source |
|---|---|---|---|---|---|---|---|
| | | Towns | | | | | Towns |

Procedure

A 2L flange necked flask was equipped with an overhead mechanical stirrer (paddle), thermometer, pressure equalised dropping funnel and nitrogen blanket. The flask was charged with 30.0 g of the chloroalcohol of formula (2) and 1200 ml of toluene to form a slurry. 30.6 g of TPP and 20.2 g of PNBA were then added and the mixture stirred at 18–20° C. 24.6 g of DIAD was dripped into the flask over a 5 min period, resulting in an exotherm to 25° C. Once all the DIAD had been added, stirring was continued for 2 hr to give a yellow solution. This solution was transferred to a rotary evaporator and the bulk of the toluene was distilled at approximately 100 mbar and 60° C. The residual yellow oil was taken up in 450 ml of ethanol and the solution was heated to 70° C. 180 ml of water were added in portions maintaining a temperature of >65° C. Care was taken, by means of gradual addition of the water over ten minutes, during water addition to prevent oiling of the product. The solution was cooled to 50° C. and seeded with product to induce crystallisation. The slurry was cooled to 10° C. with the bulk of the product crystallising at 45–50° C. The product was filtered through Whatman 54 paper and the cake was washed with 100 ml of ethanol/water mixture at 0–5° C. and dried under vacuum at 200 mbar, at 50–60° C. for 18 hr to furnish 31.0 g (i.e. a 71% yield) of product as fine white needles. A second crop of crystals (1.2 g, giving a total yield of 74%) was isolated from the mother liquors. The product was analysed by thin layer chromatography (one spot pure) and [1] H nmr which showed essentially clean product with trace impurities of triphenylphosphine oxide and DIAD-H2 (both estimated at <0.5%).

Example 2

The reaction scheme of Example 1 was followed but using a THF solvent instead of toluene.

| Chemical | Crude Mass/Vol | Strength | 100% Strength | MW | Moles | Molar Equiv | Source/Lot |
|---|---|---|---|---|---|---|---|
| 2S, 3S, chloroalcohol | 100.0 g | 97.7% LC | 98.0 g | 300 | 0.327 | 1.0x | Synthesised according to J. Org. Chem 1994, 59, 3656 |
| THF | 500 ml | >99% | 500 ml | 72 | — | — | Petrochem 16/03 pre-sample |
| TPP | 103.8 g | 99% | 103.8 g | 262 | 0.392 | 1.2x | PCL 00722 |
| PNBA | 66.1 g | >99% | 65.6 g | 167 | 0.392 | 1.2x | PCL 00728 |
| DIAD | 83.4 g | 95% | 79.2 g | 202 | 0.392 | 1.2x | Schwizerhall 292-210-3288 |
| Ethanol 18 | 600 ml | Absolute | 600 ml | 46 | — | — | Shell 982437- |
| Water | 600 ml | Towns | 600 ml | 18 | — | — | Towns |
| Ethanol:water | 2 x 500 ml | 1:1 | 84 ml | — | — | — | As above |

Procedure

A 1L flange necked flask was equipped with an overhead mechanical stirrer (paddle), thermometer, pressure equalized dropping funnel and nitrogen blanket. The flask was charged with 2S, 3S Boc-chloroalcohol (100.0 g). THF (500ml) was added to form a slurry (KF 0.0805%). TPP (103.8 g) and PNBA (66.1 g) were sequentially added to the slurry and the slurry was stirred at 18–25C. DIAD (83.4 g) was dripped in via the dropping funnel over 20 min (4.2 g/min) maintaining the exotherm at 18–20C. On full addition, stirring was continued at between 18–20C for 2 hr when the slurry had dissolved up to an olive coloured solution. The solution was quenched into ethanol (600 ml) over 35 min (40 g/min) with stirring at 18–20C resulting in crystallization of product. The slurry was then stirred for 60 min at 5–10C. The slurry was filtered (54 μpaper), 150 mm diameter, vacuum 700 mbar, cake depth 40 mm, filtration time 14 m30 s) and the cake washed with 1:1 ethanol:water (2×500 ml). The solid was dried on the filter overnight to give 119 g of 14.5% KF solid, dry weight equivalent 102.3 g. 99.0% area % HPLC, 69% molar yield.

EXAMPLE 3

The esterified product of Example 1 or Example 2 was recrystallised as follows.

Reagents

| Reagents | Mass | Strength | 100% Strength | MW | Moles | Eq. | Source |
|---|---|---|---|---|---|---|---|
| 2R, 3S Nitro ester | 29.8 g | 99% (assumed) | 29.7 g | 449 | 0.0663 | 1.0× | From Example 1 |
| Ethanol | 300 ml | Absolute | 300 ml | 85 | — | — | Hays DEB 100 |
| Water | 80 ml | Towns | 80 ml | 18 | — | — | Towns |
| Ethanol/water | 100 ml | Absolute/ Towns | 1:1 | — | — | — | Hays DEB 100/Towns |

Procedure

A 1L flange necked flask was equipped with overhead mechanical stirrer (paddle) condenser, thermometer and nitrogen blanket The flask was charged with 29.8 g of ester and 300 ml of ethanol and heated to 70–75° C. until the ester was fully dissolved. Water was added in portions (causing turbidity) maintaining a temperature of >70° C. On full addition of the water the solution was heated for a further 10 min to give a pale yellow solution. The solution was cooled to 60° C., seeded with the product to induce crystallisation and slowly cooled to 10° C. over a period of 1 hr with the bulk of the product crystallising at 45–50° C. After stirring for 30 min at 10° C. the slurry was filtered through Whatman 54 paper and the cake was washed with 100ml of ethanol/ water mixture at 0.5° C. and dried under vacuum at 50–60° C., 200 mbar for 18 hr to give 28.8 g (a 97% yield) of product as fine white needles. Thin layer chromatography analysis and $^1$H nmr demonstrated that the ester was uncontaminated with triphenylphosphineoxide and DIAD-H2 impurities.

EXAMPLE 4

The recrystallised, esterified product from Example 3 was cyclised according to the following reaction scheme:

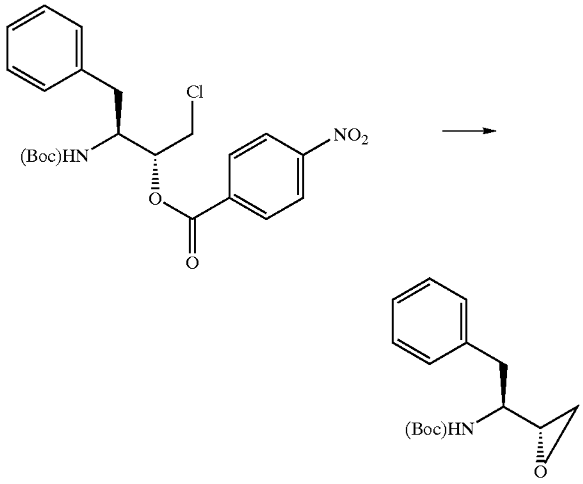

Reagents

| Reagents | Mass | Strength | 100% Strength | MW | Moles | Eq. | Source |
|---|---|---|---|---|---|---|---|
| 2R, 3S Nitro ester | 30.0 g | 100% (assumed) | 30.0 g | 449 | 0.0668 | 1.0× | Example 2 |
| Ethanol | 1020 ml | Absolute | 1020 ml | 85 | — | — | Hayman B100 |
| KOH/water | 125 ml | 0.15 g/ml | 18.8 g | 40 | 0.47 | 7.0× | Aldrich MS09811ES |
| Water | 1000 ml | Towns | 1000 ml | 18 | — | — | Towns |
| MDC | 700 ml | LC grade | 700 ml | 92 | — | — | Baker 9930020017 |
| Citric acid | 300 ml | 5% | 15.0 g | 192 | 0.078 | — | Plant |
| $NaHCO_3$ | 300 ml | 5% | 15.0 g | 84 | 0.178 | — | Aldrich 8116018 |
| Water | 300 ml | Towns | 300 ml | 18 | — | — | Towns |

Procedure

A 3L flange necked flask was equipped with an overhead mechanical stirrer (addle), thermometer, pressure equalised dropping funnel and nitrogen blanket. The flask was charged with 30.0 g of ester and 1020 ml of ethanol to form a slurry.

The slurry was cooled to 0–5° C. and 125 ml of KOH solution were added over a 5 min period maintaining the temperature at <5° C. On full addition the reaction was monitored by HPLC and was complete after 3 hr. The reaction was quenched with water (1000 ml), stirred for 5 min and extracted twice with MDC (once with 500 ml of MDC and then once with 200 ml of MDC). The combined organic extracts were washed with 300 ml of 5% citric acid, 300 ml of 5% $NaHCO_3$ and 300 ml of water. The product solution was dried in the presence of anhydrous sodium sulphate, filtered and concentrated on a rotary evaporator at 50° C. from 50–85 mbar to give 17.7 g (i.e. >95% yield) of a clear oil that slowly solidified on refrigeration, having a melting point of 49° C. The isolated product was >99% pure by area HPLC with no 2S,3S diastereomer observed. $^1$H nmr of the product confirmed the structure.

EXAMPLES 5 to 14

The following table shows summary procedures and results of further esterification reactions according to the invention. Unless otherwise specified, the procedures and conditions were similar to those mentioned above in Example 1.

| Example | Input chloroalcohol | Scale | Reagent charge | Procedure | Work-up | Estimated Purity | Yield |
|---|---|---|---|---|---|---|---|
| 5 | 98.3% 2S, 3S 0.7% 2R, 3S | 2.0 g | Toluene 70 ml DEAD 1.2× $PPh_3$ 1.2× PNBA 1.2× | Add DEAD over 1 min then stir at 20° C. for 2 hr | Concentrate to oil then column chromatography | 98% (nmr) | 78% |
| 6 | 96.3% 2S, 3S 2.2% 2R, 3S | 2.0 g | Toluene 100 ml DIAD 1.2× $PPh_3$ 1.2× PNBA 1.2× | Add DIAD over 1 min then stir at 20° C. for 2 hr | Concentrate to oil then column chromatography | 98% (nmr) | 82% |
| 7 | 98.3% 2S, 3S 0.7% 2R, 3S | 8.0 g | Toluene 250 ml DEAD 1.2× $PPh_3$ 1.2× PNBA 1.2× | Add DEAD over 1 min then stir at 20° C. for 2 hr | Concentrate to oil, dissolve in ethanol (100 ml) then crystallise | 95% (nmr) Trace $OPPh_3$ | 48% |
| 8 | 96.3% 2S, 3S 2.2% 2R, 3S | 10.0 g | Toluene 250 ml DIAD 1.2× $PPh_3$ 1.2× PNBA 1.2× | Add DIAD over 5 min then stir at 20° C. for 2 hr | Concentrate to oil, dissolve in ethanol (100 ml) then crystallise (2 crops) | 95% (nmr) Trace $OPPh_3$ | 67% |
| 9 | 96.3% 2S, 3S 2.2% 2R, 3S | 5.0 g | Toluene 200 ml DIAD 1.2× $PPh_3$ 1.2× PNBA 1.2× | Add DIAD over 5 min then stir at 20° C. for 2 hr | Concentrate to oil, dissolve in ethanol (75 ml) then water added (300 ml) at 70–80° C., cool and crystallise | 98% (nmr) Trace $OPPh_3$ DIAD-H2 contamination | 75% |
| 10 | 96.9% 2S, 3S 0.8% 2R, 3S | 30.0 g | Toluene 1200 ml DIAD 1.2× $PPh_3$ 1.2× PNBA 1.2× | Add DIAD over 5 min then stir at 20° C. for 2 hr | Concentrate to oil, dissolve in ethanol (450 ml) then water added (200 ml) at 70–80° C., cool and crystallise | 98% (nmr) Trace $OPPh_3$ DIAD-H2 contamination | 67% |
| 11 | 98.8% 2S, 3S 0.9% 2R, 3S | 60.0 g | Toluene 2400 ml DIAD 1.2× $PPh_3$ 1.2× PNBA 1.2× | Add DIAD over 10 min then stir at 20° C. for 2 hr | Concentrate to oil, dissolve in ethanol (900 ml) then water added (360 ml) at 70–80° C., cool and crystallise | 98% (nmr) Trace $OPPh_3$ DIAD-H2 contamination | 74% |
| 12 | 97.8% 2S, 3S, 08.% 2R, 3S | 25.0 g | Dimethoxyethane 250 ml DIAD 1.4×, PPh3 1.4×, PNBA 1.4× | Add DIAD over 10 min Then 2 hr stir it 20° C. | Add reaction mixture to ethanol (200 ml) and water (200 ml), filter resulting solid | 98% (nmr) Trace OPPh3 and DIAD-h2 contamination | 72% |
| 13 | 97.7% 2S, 3S, 1.0% 2R, 3S | 25.0 g | Tetrahydrofuran 125 ml DIAD 1.2×, PPh3 1.2×, PNBA 1.2× | Add DIAD over 20 min Then 2 hr stir at 20° C. | Add reaction mixture to ethanol (220 ml) and water (300 ml), filter resulting solid | 90% (nmr) Residual TPPO | 68% |
| 14 | 97.7% 2S, 3S 1.0% 2R, 3S | 100 g | Tetrahydrofuran 500 ml DIAD 1.2×, PPh3 1.2×, PNBA 1.2× | Add DIAD over 20 min Then 2 hr stir at 20° C. | Add reaction mixture to ethanol (600 ml) and water (600 ml), filter resulting solid | 99.0% (HPLC) | 69% |

EXAMPLES 15 to 17

The following table shows summary results of further examples of the recrystallisation step according to the invention. Unless otherwise specified, the procedures and conditions used are similar to those specified above in connection with Example 3.

| Example | Input Ester | Input Quality | Scale | Reagent Charge | Procedure | Estimated Purity | Yield |
|---|---|---|---|---|---|---|---|
| 15 | From Example 5 | Trace $OPPh_3$ and DEAD-H2 contamination by nmr | 2.3 g | 23 ml ethanol | Heat to dissolve, cool and filter. Thick mixture | Free of impurities by nmr CHN fits | 74% |
| 16 | A blend | Trace $OPPh_3$ and DEAD-H2 contamination by nmr | 14.7 g | 147 ml ethanol | Heat to dissolve, cool and filter. Thick mixture | Free of impurities by nmr | 78% |
| 17 | From Example 11 | Trace $OPPh_3$ and DIAD-H2 contamination by nmr | 65.7 g | 600 ml ethanol 160 ml water | Heat ester in ethanol to dissolve, then add water at 70–75° C., cool and filter | Free of impurities by nmr | 95% |

EXAMPLES 18 to 23

The following table shows in summary form further examples of the cyclisation step according to the invention. Unless otherwise specified, the procedures and conditions are similar to those specified above in connection with Example 4.

| Example | Input Ester | Scale | Reagent charge | Procedure | Work-up | Estimated Purity | Yield |
|---|---|---|---|---|---|---|---|
| 18 | Recrystallised ester | 200 mg | Ethanol 25 ml KOH 30× | Add aqueous KOH to ethanol slurry of the ester. Monitor reaction progress by LC. Complete after 1 hr at 0–2° C. | Neutralise with citric acid and concentrate on RFE. Dissolve in MDC, acid base wash, dry and concentrate to oil that solidifies on refrigeration | >99% 2R, 3S by LC. No 2S, 3S isomer observed. Pure by nmr | 79% |
| 19 | Recrystallised ester | 5.0 g | Ethanol 200 ml KOH 7× | Add aqueous KOH to ethanol slurry of the ester. Monitor reaction progress by LC. Complete after 3.5 hr at 0–2° C. | Neutralise with citric acid and concentrate on RFE. Dissolve in MDC, acid base wash, dry and concentrate | 0.8% $OPPh_3$ 98.9% 2R, 3S 0.2% alcohol | 88% |
| 20 | Isolated ester from Example 9 | 3.0 g | Isopropanol 120 ml KOH 5.0× | Add aqueous KOH to slurry of the ester. Monitor reaction progress by LC. Complete after 3.5 hr at 0–2° C. | Neutralise with citric acid and concentrate on RFE. Dissolve in MDC, acid base wash, dry and concentrate | 7.6% imp 82.4% 2R, 3S 9.52% imp | 74% |
| 21 | Recrystallised ester from Example 9 | 3.0 g | Ethanol 120 ml KOH 7× | Add aqueous KOH to ethanol slurry of the ester. Monitor reaction progress by LC. Complete after 3.5 hr at 0–2° C. | Neutralise with citric acid and concentrate on RFE. Dissolve in MDC, acid base wash, dry and concentrate | 99.8% 2R, 3S 0.1% alcohol | 95% |
| 22 | Recrystallised ester from Example 17 | 25.0 g | Ethanol 1000 ml KOH 7× (105 ml) | Add aqueous KOH to ethanol slurry of the ester. Monitor reaction progress by LC. Complete after 3 hr at 0–2° C. | Neutralise with citric acid and concentrate on RFE to half volume. Dissolve in MDC, acid base wash, dry and concentrate | 0.4% 2S, 3S or $OPPh_3$ 99.6% 2R, 3S | >95% |
| 23 | Isolated ester from Example 10 | 25.0 g | Ethanol 1000 ml KOH 7× (105 ml) | Add aqueous KOH to ethanol slurry of the ester. Monitor reaction progress by LC. Complete after 3 hr at 0–2° C. | Neutralise with citric acid and concentrate on RFE to half volume. Dissolve in MDC, acid base wash, dry and concentrate | 1.0% 2S, 3S or $OPPh_3$ 99.6% 2R, 3S | >95% |

What is claimed is:

1. A process for producing an optically active (2R, 3S)-epoxide of the formula (1):

(1)

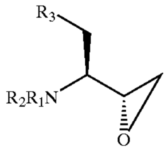

or its enantiomer wherein each of $R_1$ and $R_2$ is independently selected from the group consisting of hydrogen, optionally substituted alkyl, aryl, aralkyl, and alkaryl groups, and amine-protecting groups, and $R_3$ is selected from hydrogen and optionally suitably protected alkyl, cycloalkyl, aryl, aralkyl and alkaryl groups, said process comprising subjecting an optically active (2S,3S)-alcohol of formula (2):

(2)

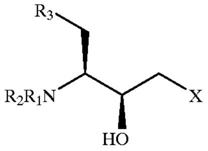

or its enantiomer, wherein X is a leaving group, to a Mitsunobu reaction to obtain a Mitsunobu reaction product and cyclising the Mitsunobu reaction product to form an optically active (2R,3S) epoxide of the general formula (1), the stereochemistry of the optically-active (2S,3S)-alcohol or its enantiomer being inverted in said Mitsunobu reaction.

2. The process of claim 1, further comprising recrystallising the Mitsunobu reaction product prior to cyclising.

3. The process of claim 1 is wherein the compound of formula (2) is reacted with a phosphine and an azodicarboxylate under acid conditions to form an intermediate ester of formula (3):

(3)

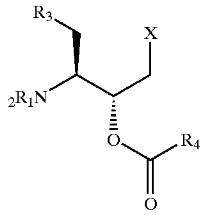

wherein $R_4$ is an optionally nitrogenated alkyl, aryl, aralkyl or alkaryl group.

4. The process of claim 2, wherein the compound of formula (2) is reacted with a phosphine and an azodicarboxylate under acid conditions to form an intermediate ester of formula (3):

(3)

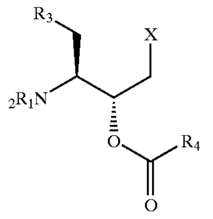

wherein $R_4$ is an optionally nitrogenated alkyl, aryl, aralkyl or alkaryl group.

5. The process of claim 3, wherein the phosphine comprises triphenylphosphine.

6. The process of claim 3, wherein the azodicarboxylate is diisopropylazodicarboxylate.

7. The process of claim 5, wherein the azodicarboxylate is diisopropylazodicarboxylate.

8. The process of claim 3, wherein the acid conditions are provided by a carboxylic acid.

9. The process of claim 5, wherein the acid conditions are provided by a carboxylic acid.

10. The process of claim 6, wherein the acid conditions are provided by a carboxylic acid.

11. The process of claim 8, wherein the carboxylic acid is paranitrobenzoic acid.

12. The process of claim 1, wherein said Mitsonubo reaction takes places in the presence of a solvent comprising at least one of toluene and tetrahydrofuran.

13. The process of claim 2, wherein said step of recrystallizing takes place in a recrystallizing solvent comprising ethanol and water.

14. The process of claim 2, wherein said cyclization is effected by a base, following said step of recrystallizing.

15. The process of claim 14, wherein said base comprises aqueous KOH and said cyclization takes place in ethanol.

16. The process of claim 1, wherein said amine protecting group is butoxy/carbonyl.

17. The process of claim 1, wherein said optically active (2S,3S)-alcohol is a haloalcohol.

* * * * *

UNITED STATES PATENT AND TRADEMARK OFFICE

CERTIFICATE OF CORRECTION

PATENT NO. : 6,693,205 B2

DATED : February 17, 2004

INVENTOR(S) : David Edward Justice

It is certified that error appears in the above-identified patent and that said Letters Patent is hereby corrected as shown below:

Column 13,
Line 66, after Formula (1) and prior to Formula (2), insert the following paragraph:
-- or its enantiomer wherein each of $R_1$ and $R_2$ is independently selected from the group consisting of hydrogen, optionally substituted alkyl, aryl, aralkyl, and alkaryl groups, and amine-protecting groups, and $R_3$ is selected from hydrogen and optionally suitably protected alkyl, cycloalkyl, aryl, aralkyl and alkaryl groups, said process comprising subjecting an optically active (2S,3S)-alcohol of --

Signed and Sealed this

Eighth Day of June, 2004

JON W. DUDAS

*Acting Director of the United States Patent and Trademark Office*